(12) United States Patent
Azzopardi et al.

(10) Patent No.: US 11,453,905 B2
(45) Date of Patent: Sep. 27, 2022

(54) METHOD OF DETECTING BACTERIAL INFECTION IN A BIOLOGICAL SAMPLE

(71) Applicant: Trubac Ltd., Qrendi (MT)

(72) Inventors: Ernest A. Azzopardi, Qrendi (MT); Rosa Sofia Rodrigues Teixeira, Cork (IE)

(73) Assignee: Trubac, LTD., Qrendi (MT)

( * ) Notice: Subject to any disclaimer, the term of this patent is extended or adjusted under 35 U.S.C. 154(b) by 192 days.

(21) Appl. No.: 16/094,325

(22) PCT Filed: Apr. 14, 2017

(86) PCT No.: PCT/GB2017/000058
§ 371 (c)(1),
(2) Date: Oct. 17, 2018

(87) PCT Pub. No.: WO2017/182765
PCT Pub. Date: Oct. 26, 2017

(65) Prior Publication Data
US 2019/0119720 A1   Apr. 25, 2019

(30) Foreign Application Priority Data

Apr. 18, 2016 (GB) ..................... 1606732

(51) Int. Cl.
| | |
|---|---|
| *C12Q 1/40* | (2006.01) |
| *C12Q 1/06* | (2006.01) |
| *G01N 33/569* | (2006.01) |
| *C12Q 1/04* | (2006.01) |

(52) U.S. Cl.
CPC ............. *C12Q 1/40* (2013.01); *C12Q 1/04* (2013.01); *C12Q 1/06* (2013.01); *G01N 33/56911* (2013.01)

(58) Field of Classification Search
None
See application file for complete search history.

(56) References Cited

U.S. PATENT DOCUMENTS

2012/0309036 A1   12/2012   Gübitz et al.
2015/0004627 A1   1/2015   Wu et al.

FOREIGN PATENT DOCUMENTS

| CN | 104 237 344 A | 12/2014 |
| EP | 0 145 398 A2 | 6/1985 |
| GB | 2 426 335 A | 11/2006 |
| GB | 2 471 672 A | 1/2011 |
| WO | WO 1997/29366 A1 | 8/1997 |

(Continued)

OTHER PUBLICATIONS

Kejriwal et al., J. Clin. Diagn. Res. 8(10): ZC56-ZC60 (2014).*

(Continued)

*Primary Examiner* — Erin M. Bowers
(74) *Attorney, Agent, or Firm* — Klarquist Sparkman, LLP

(57) ABSTRACT

A method of indicating the presence of a bacterial infection in a biological sample is provided. The method detects a marker for infection by providing a device, the device including a biosensor, an interaction arising between the biosensor and the marker when the marker is present in the biological sample. Contacting at least a part of the biological sample with the biosensor of the device, therefore, provides analysis of the biological sample with respect to the marker by detecting for the interaction between the biosensor and the marker. A preferred marker is the enzyme amylase.

19 Claims, 9 Drawing Sheets

(56) References Cited

FOREIGN PATENT DOCUMENTS

| WO | WO 2003/040406 A2 | 5/2003 |
| WO | WO 2005/121357 A2 | 12/2005 |
| WO | WO 2010/124270 A1 | 10/2010 |
| WO | WO 2016/023943 A1 | 2/2016 |

OTHER PUBLICATIONS

Aluoch et al., Anal. Biochem. 340: 136-144 (2005).*
Santos et al., Mat. Sci. Eng. C 32: 530-535 (2012).*
Larsen et al., Laryngoscope 94: 1302-1306 (1984).*
Aluoch et al., "Development of an oral biosensor for salivary amylase using a monodispersed silver for signal amplification," *Anal Biochem.* 340:136-144, 2005.
Ghafar-Zadeh, "Wireless Integrated Biosensors for Point-of-Care Diagnostic Applications," *Sensors* 15:3236-3261, 2015.
Jin et al., "Impedimetric Dengue Biosensor based on Functionalized Graphene Oxide Wrapped Silica Particles," *Electrochimica Acta* 194:422-430, 2016.
Kejriwal et al., "Estimation of levels of salivary mucin, amylase and total protein in gingivitis and chronic periodontitis patients," *J Clin Diagn Res.* 8:ZC56-ZC60, 2014.
Smiechowski et al., "Electrochemical detection and characterization of proteins," *Biosens Bioelectron.* 22: 670-677, 2006.
Zhang et al., "Smartphone-based point-of-care testing of salivary α-amylase for personal psychological measurement," *Analyst* 140:7399-7406, 2015.
Search Report for GB 1606732.4 dated Jan. 23, 2017 (4 pages).
International Search Report and Written Opinion for PCT/GB2017/000058 dated Aug. 4, 2017 (12 pages).

\* cited by examiner

*Infected wound (experimental)*

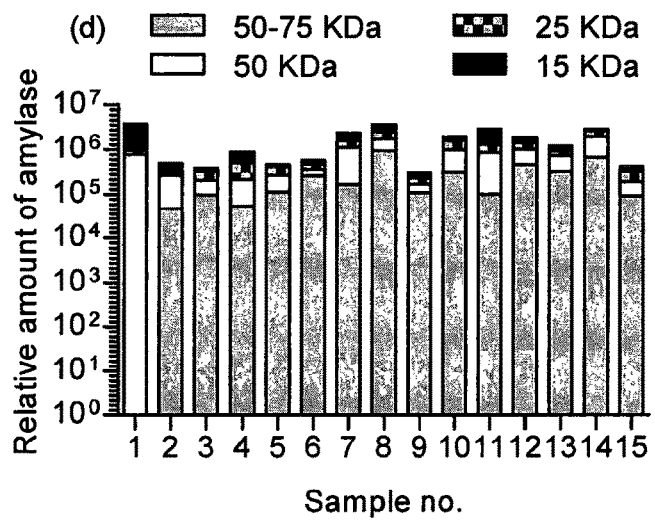
Figure 4
Figure 5
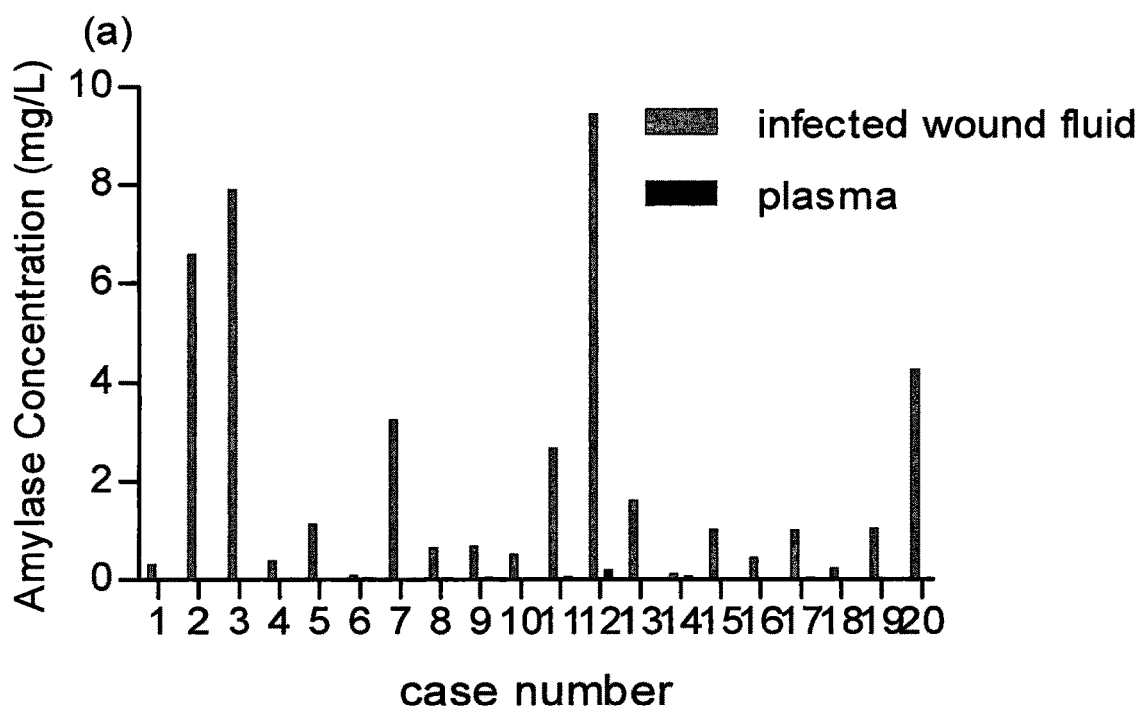

*Delta A concentration*

METHOD OF DETECTING BACTERIAL INFECTION IN A BIOLOGICAL SAMPLE

CROSS REFERENCE TO RELATED APPLICATIONS

This is the U.S. National Stage of International Application No. PCT/GB2017/000058, filed Apr. 14, 2017, which was published in English under PCT Article 21(2), which in turn claims the benefit of GB Application No. 1606732.4, filed Apr. 18, 2016.

FIELD

This invention concerns improvements in and relating to detection, particularly of the presence of a disease and/or of infection at a site, and/or improvements in and relating to transportation, particularly the transportation of pharmaceutical compounds to a site of disease and/or infection.

BACKGROUND

There are many situations where detection of infection is a significant issue. In some circumstances, the primary injury to the human body (for example a burn injury) itself causes symptoms that mimic infection. The practice of microbiological swabbing, and subsequent identification of organisms confirms their presence in a wound, but not the presence of infection. Multi-drug resistance is a clinical concern, and administering antibiotics where there might be no clinical need increases costs, and increases the well-known risks from over use of antibiotics.

EP0145398 provides one form of sensor for the detection of amylase activity for the purpose of revealing a disease which causes enhanced levels of amylase. There is no suggestion that amylase (or closely related species) is indicative of infection and so no suggestion that the detection of amylase provides for the detection of infection. The approach is limited merely to the revealing of one or a limited number of specific diseases.

GB2426335 relates to the detection of wound infection, but through the detection of reactive oxygen species. These are unrelated to amylase and so there no suggestion that amylase is indicative of infection and so no suggestion that the detection of amylase provides for the detection of infection.

US2012/0309036, WO97/29366, US2015/0004627 and WO2010/124270 all provide different types of sensors. None is for the detection of amylase and none provides that amylase is indicative of infection and so no suggestion that the detection of amylase provides for the detection of infection exists.

Approaches that do detect for bacterial infection, through very different mechanisms to the present invention, often determine the presence of bacteria and not whether the bacteria are causing infection.

SUMMARY

The present invention has amongst its potential aims to provide an improved method of analysis for a biomarker indicative of infection, particularly bacterial infection. The present invention has amongst its potential aims to provide an improved method for detection of infection, particularly bacterial infection. The present invention has amongst its potential aims an improved method for indicating the presence of infection to cause further investigations and/or further evaluation before making a clinical diagnosis and/or proposing a treatment. The present invention has amongst its potential aims to provide an improved method of analysis for a biomarker indicative of infection, particularly bacterial infection.

The present invention has amongst its potential aims to provide an improved composition for pharmaceutical use. The present invention has amongst its potential aims to provide an improved composition for the targeted delivery of a composition for pharmaceutical use.

According to a first aspect the invention provides a method of analysing a biological sample for a marker, the method comprising:

providing a device, the device including a sensor for the marker;

contacting at least a part of the biological sample with the device;

analysing the at least a part of the biological sample with respect to the marker;

indicating a characteristic of the marker using the device;

wherein the biomarker is an enzyme, preferably amylase.

The first aspect of the invention may further include that:

the method of analysing is a method of indicating the presence of infection in the biological sample; and/or the method may include the sensor being a biosensor; and/or the method may include an interaction arising between the sensor and the marker when the marker is present in the biological sample; and/or the method may further include contacting the at least a part of the biological sample with the biosensor of the device; and/or the method may further include detecting for the interaction between the biosensor and the marker;

the method may further include the characteristic being the presence or absence of the marker.

According to a second aspect the invention provides a method of indicating the presence of infection in a biological sample by investigating a marker for infection, the method comprising:

providing a device, the device including a biosensor, an interaction arising between the biosensor and the marker when the marker is present in the biological sample;

contacting at least a part of the biological sample with the biosensor of the device;

analysing the at least a part of the biological sample with respect to the marker by detecting for the interaction between the biosensor and the marker;

indicating a characteristic of the marker using the device, the characteristic being the presence or absence of the marker;

wherein the marker is an enzyme, preferably amylase.

The first and second aspects of the invention may include any of the following features, options or possibilities.

The method of analysing may be a method of diagnosis for infection.

The method of analysing may be a method of analysing for and/or detecting for and/or diagnosing elevated marker levels at a site, for instance elevated levels compared with an experimentally obtained baseline. The method of analysing may be a method of analysing for and/or detecting for and/or diagnosing elevated marker levels at a site, for instance elevated levels compared with an experimentally obtained baseline, arising from infection at a site. The method of analysing may be a method of analysing for and/or detecting for and/or diagnosing elevated marker levels at a site, for instance elevated levels compared with marker levels at another location of the same patient, such as the blood. The method of analysing may be a method of analysing for and/or detecting for and/or diagnosing elevated marker levels at a site, for instance elevated levels compared with marker levels at another location of the same patient, such as the blood, the elevated level arising from infection at a site.

The method of analysing may be a method of quantifying the amount of the marker in the at least a part of the biological sample. The method may quantify the activity of the marker. The method may quantify the concentration of the marker. The method may quantify the activity of the marker relative to the activity of the marker in a reference sample. The method may quantify the concentration of the marker relative to the concentration of the marker in at least a part of a reference sample.

The reference sample may be another biological sample taken from the same source, for instance the same human or animal. The reference sample is preferable taken from another site on the source to the site being analysed, for instance for infection. The other site may be a vein. The reference same may be a biological sample in which the presence or amount of the marker is not influenced by the presence of infection at the site being analysed. The reference sample may be an intravascular fluid, such as whole blood or any of the separated components of blood, for example serum or plasma. One or more of the separated components may be considered.

The biological sample may be body fluids and/or cells and/or processed cells and/or a tissue sample taken from the site to be analysed. The biological sample may be extracted from an item which has been in proximity with the site to be analysed, such as a dressing, pad, compress, swab, skin substitutes, biomembrane. The biological sample may be taken from inside and/or outside the body.

The site may by on the exterior of a body and/or the site may be interior to a body. The site may be a surgical site, including a plastic surgery site. The site may be a disease site and/or a pathology site. The site may be an infection site. The site may be an injury site. The site may be a wound, for instance an open wound such as a tear, cut, puncture, incision, laceration, abrasion, avulsion, penetration or gunshot wound or for instance a closed wound such as a contusion, hematoma or crush injury. The site may particularly be a burn. The site may be superficial or it may be deep, and in any layer, tissue, organ or bodily fluid.

The infection may be a bacterial infection. A bacterial infection may be defined as a proliferation of bacteria on or inside a human or animal which causes harm to the human or animal. The bacterial infection may be homogeneous or heterogeneous. The bacterial infection may be localised to one or more sites or systemic. The bacterial infection may be symptomatic or asymptomatic.

Preferably the method is distinguishing for bacterial infection.

Preferably the method is distinguishing between bacterial infection and inflammation.

The method may provide sensitivity to bacterial infection. The sensitivity may be greater than 80%, preferably greater than 85%, more preferably greater than 90% and ideally 98% or more.

The method may provide specificity with respect to the absence of bacterial infection. The specificity may be greater than 75%, preferably greater than 80%, more preferably greater than 85% and ideally 90% or more.

The infection may be caused by Gram positive (such as *Staphylococcus* spp.) and/or Gram negative organisms (such as *Acinetobacter* spp.). The infection may be caused aerobic and/or micro-aerobic organisms (such as *Streptococcus* sp.) and/or anaerobic organisms (such as *Clostridium* spp.). The infection may be mono-microbial or poly-microbial. The infection may be a poly-microbail infection which is synergistic or non-synergistic. The infection may be one or more of: Steptococci, such as *Streptococcus pyrogenesi*, and/or Enterococci, such as *Enterococcus faecalis*, and/or Staphylococci, such as *Staphylococcus aureus*, and/or *Pseudomonas*, such as *Pseudomonas aeruginosa, Enterobacter, Escherichia coli, Klebsiella, Bacillus*, such as *B. cerus, Clostridium*, such as *C. perfringens, C. teanii, C. difficile, Proteus, Bacteroides, Clostridium*.

The marker is preferably an enzyme which is a catalyst for the hydrolysis of starch into sugars. The marker may be a glycoside hydrolase. The marker is most preferably amylase. The marker may be one or more or all of a mixture of enzymes. The marker is preferably produced by the human or animal from which the biological sample is obtained. The marker is preferably an enzyme which is a catalyst for the hydrolysis of starch into sugars produced by the human or animal from which the biological sample is obtained. The marker may be a glycoside hydrolase preferably produced by the human or animal from which the biological sample is obtained. The marker is most preferably amylase preferably produced by the human or animal from which the biological sample is obtained. The marker may be one or more or all of a mixture of enzymes preferably produced by the human or animal from which the biological sample is obtained.

The device may have a separate existence outside of the limitations of the method and purpose of the method.

The device may include the sensor together with one or more or all of, a power source, control electronics, a computer processor, computer memory, a user interface, a user viewable display, a signal output connection, a signal input connection.

The device is preferably a self-contained unit. The device is preferably portable. The device may be hand-held and/or desk-top.

The sensor may be screen printed on to a part of the device and/or a sensor support. The sensor may detect the marker without the use of labels for the marker. The sensor may be an immunosensor. The sensor is preferably a graphene based sensor.

The sensor may include an aromatic amine, such as aniline, on a support. The support may be a graphene support, gold support, zinc oxide support, iron oxide support or other forms of carbon support. Electropolymerisation of the aromatic amine, such as aniline, onto the sensor support is preferred, for instance to achieve increased sensitivity and/or lower limits of quantification. The sensor may be constructed by in situ electropolymerization of the aromatic amine, such as aniline, onto a graphene support.

The sensor may include an enzyme antibody, preferably an enzyme specific antibody. The sensor may include a glycoside hydrolase antibody, preferably a glycoside hydrolase specific antibody. The sensor may include an amylase antibody, preferably an amylase specific antibody. Preferably the sensor includes an α-amylase antibody, most preferably an α-amylase specific antibody.

The sensor may be constructed by covalently binding the enzyme specific antibody to a layer. The layer may be a transducer layer. The layer may be a conductive polymer layer, such as a polyaniline layer.

The transducer layer may be separate from a control electronics layer, may be integrated there with or may be the same layer. The control electronics layer may be a controlling device assembly.

The control electronics, such as a controlling device assembly, may use electrochemical impedance spectroscopy to analyse for and/or detect for and/or indicate the marker. The control electronics, such as a controlling device assembly, may use variation in the dielectric properties of the at least a part of the sample and/or the sensor as a function of frequency.

The detecting for the interaction may use electrochemical impedance spectroscopy. The detection for the interaction may use variation in the dielectric properties of the at least a part of the sample and/or the sensor as a function of frequency. The sensor differs from previous electrochemical impedance spectroscopy based sensors by using electropolymerization in the construction of the sensor and/or in terms of the sensor being used to determine the presence of bacterial infection through the detection of amylase.

Preferably the electrochemical impedance spectroscopy has a linear response against α-amylase concentration. A linear response may be considered to be a response which deviates no more than 10% from linear.

Preferably electrochemical impedance spectroscopy generates a signal output when the marker is present in the at least part of the sample. Preferably the signal output varies with activity of the marker and/or concentration of the marker, ideally in a linear response.

The sensor may detect concentrations of the marker, preferably in a simulated biological sample, biological sample or human plasma, as low as 100 International Units/L ° U/L), preferably as low as 50 International Units/L (IU/L), more preferably as low as 10 International Units/L (IU/L), and ideally as low as International Units/L (IU/L). The sensor may have a limit of detection as low as 1 U/L, preferably as low as 0.4 U/L, more preferably as low as 0.1 U/L and ideally as low as 0.025 U/L and possibly even as low as 0.01 U/L.

The sensor may display a linear response to increasing α-amylase concentration between 1 and 1000 International Units/L (IU/L), and/or a limit of detection of 0.025 U/L and possibly even as low as 0.01 U/L.

The contacting of the at least a part of the sample with the sensor may be provided by placing the sample on the sensor and/or dipping the sensor in the sample and/or inserting the sample into the device.

The characteristic may be the presence of the marker. The characteristic may be the absence of the marker. The characteristic may be the level of the marker, for instance absolutely and/or relative to one or more predetermined thresholds. The characteristic may be the quantity of the marker. The quantity of the marker may be the activity of the marker and/or the concentration of the marker.

The characteristic may be the level of the marker in a sample taken from one type of site compared with the level of the marker in a sample taken from another type of site. The characteristic may be the difference between the level of the marker in a sample taken from one type of site compared with the level of the marker in a sample taken from another type of site. The characteristic may be the quotient of the level of the marker in a sample taken from one type of site to the level of the marker in a sample taken from another type of site and/or vice versa.

The characteristic may be expressed in terms of activity and/or concentration of the marker.

The one type of site may be the infection site or potential infection site. The another type of site may be a site distal from the one type of site in the same patient. The another type of site may be a blood or plasma source. The another type of site may be associated with the same patient as the one type of site, but the another type of site may be from a control or reference individual or group of individuals.

The characteristic may be outputted from the device. The output may be a visual display to the user. The output may be an electronic signal and/or electrochemical signal. The output may be a permanent recording of the characteristic.

The method of analysis may include a method for detecting the presence of infection. The method of analysing may include a method of detecting the type of infection. The type of infection may be with respect to a classification of the source of infection, for instance Gram negative or Gram positive. The type of infection may be with respect to the classification of the source of the infection, for instance bacterial, most preferably bacterial only, with possibilities for viral, fungal, protazoal. The type of infection may be with respect to the characterisation of the genus of the source of the infection, for instance one or more selected from the group: Steptococci, Enterococci, Staphylococci, *Pseudomonas, Enterobacter, Klebsiella, Bacillus, Clostridium*. The type of infection may be with respect to the characterisation of the species of the source of the infection, for instance one or more selected from the group: *Streptococcus pyrogenesi, Enterococcus faecalis, Staphylococcus aureus, Pseudomonas aeruginosa, Escherichia coli, Bacillus cerus, Clostridium perfringens, Clostridium teanii, Clostridium difficile*.

The method may be a method of verifying that the marker is present at a site, such that the marker can activate a pharmaceutical compound when the pharmaceutical compound is present at the site. The method may include a method of predicting and/or estimating the activation rate of a pharmaceutical compound at a site by the marker. This is a useful addition to situations in which an inactive form may convert to the active form because the marker, for instance amylase, causes the active compound to be rendered pharmaceutically active, for instance by causing breakdown of the inactive form.

The method may be a method of investigating a site to establish that the marker is preferentially present at the site, such that transportation of a pharmaceutical compound as part of a combination with the marker, such as amylase, to the site occurs.

According to a third aspect the invention provides a composition comprising a pharmaceutical compound combined with a carrier constituent, the carrier constituent comprising amylase.

According to a fourth aspect the invention provides a composition comprising a pharmaceutical compound combined with a carrier constituent, the carrier constituent comprising an enzyme.

The enzyme is preferably a catalyst for the hydrolysis of starch into sugars. The enzyme may be a glycoside hydrolase. Most preferably the enzyme is amylase. A mixture of enzymes may be provided.

According to a fifth aspect of the invention there is provided a method of treatment comprising administering to a human or animal of a composition comprising a pharmaceutical compound combined with a carrier constituent, the carrier constituent comprising amylase.

The method of treatment may be a method of treating infection and/or preventing infection. The method of treatment may be for a human or animal with burns.

The third and/or fourth and/or fifth aspects of the invention may include any of the following features, options and possibilities.

The pharmaceutical compound may be a pharmaceutically active compound. The pharmaceutical compound may be pharmaceutically active compound whilst combined with the carrier constituent. The pharmaceutical compound may be pharmaceutically active compound after being separated from the carrier constituent. The pharmaceutical compound may be a pharmaceutically in-active compound. The pharmaceutical compound may transition from being a pharmaceutically in-active compound to a pharmaceutically active compound due to an event. The event may be the passage of time and/or becoming separated from the carrier constituent and/or interaction with another compound.

The pharmaceutical compound may be combined reversibly. The pharmaceutical compound may be combined irreversibly.

The pharmaceutical compound may be combined with the carrier constituent, by being combined directly with the amylase. The pharmaceutical compound may be combined directly with the amylase by linking the pharmaceutical compound with the amylase. The linking may be covalent linking. The linking may be cross-linking. The linking may be covalent binding. The linking may be ionic binding.

The pharmaceutical compound may be combined with the carrier constituent, by being combined directly with an intermediary. The combination of the pharmaceutical compound with the intermediate may be irreversible or reversible. The intermediary may be combined directly with the amylase. The pharmaceutical compound may be combined directly with the intermediary and/or the intermediary may be combined directly with the amylase by linking. The linking may be the same or different with respect to the two links. The linking may be covalent linking. The linking may be cross-linking. The linking may be covalent binding. The linking may be ionic binding.

The combination of the pharmaceutical compound with the carrier constituent may be irreversible or reversible. The pharmaceutical compound can preferably be released from the combination with the carrier constituent. The pharmaceutical compound may be inactive or the activity may be impaired or inhibited when in combination with the carrier constituent. Preferably the pharmaceutical compound is not impaired or inhibited in its activity when released from the combination with the carrier constituent and/or when the linking is reversed.

The intermediary may be a cross-linking compound. The pharmaceutical compound may be bound directly to amylase. This can be provided by a variety of mechanisms including but not only, zero-length cross linking. The pharmaceutical compound may be bound to an intermediary which is then itself bound to amylase. The intermediary may be non-biodegradable, for example poly(ethylene) glycol, or may be biodegradable.

The pharmaceutical compound may treat or prevent infection, particularly bacterial infection. The pharmaceutical compound may treat or prevent infection by, amongst others, Steptococci, such as *Streptococcus pyrogenesi*, and/or Enterococci, such as *Enterococcus faecalis*, and/or Staphylococci, such as *Staphylococcus aureus*, and/or *Pseudomonas*, such as *Pseudomonas aeruginosa*, *Enterobacter*, *Escherichia coli*, *Klebsiella*, *Bacillus*, such as *B. cerus*, *Clostridium*, such as *C. perfringens*, *C. teanii*, *C. difficile*, *Proteus*, *Bacteroides*, *Clostridium*.

The pharmaceutical compound may one or more of, including combinations of: antibiotics, analgesics, opioids, anti-inflammatories, antihistamines.

The pharmaceutical compound may be used to deliver therapy in multiple modalities, alone or in combination.

The pharmaceutical compounds may include targeted pharmacotherapy and/or targeted radiologically active compounds and/or compounds activated by light, chromophores, and/or compounds activated by sound, such as ultrasound. The pharmaceutical compound may include compounds acting through emission or through their response to emissions, as opposed to just a pharmaceutical chemical interaction.

One or more different pharmaceutical compounds may be provided in the composition.

The composition may be a parenteral administered composition, for instance for injection, including sub-cutaneous, intramuscular, intravenous, intra-arterial, intrathecal, intra-peritoneal injection. The composition may be an enteral administered composition, for instance for oral administration. The composition may be provided in a medicinal product.

The medicinal product is preferably altered in the patient to present the composition in an absorbable form. For instance, the medicinal product may disintegrate during ingestion and/or in the stomach and/or in the intestine to present the composition in an absorbable form. The composition in the absorbable form preferably still comprises the pharmaceutical compound combined with a carrier constituent, the carrier constituent comprising amylase.

The composition in the absorbable form, preferably still comprising the pharmaceutical compound combined with a carrier constituent, the carrier constituent comprising amylase, preferably remains in the combined form for a time period which provides for a proportion of the combined form to be transported to the site to be treated. The proportion of the composition which remains in the combined form may be at least 25% of the total composition after the time period. The proportion is more preferably greater than 40%, for instance greater than 50% of even greater than 70%. The time period may be defined as the time of the peak concentration point at the site being treated. The time period may be defined as at least 2 hours after administration.

Particularly when administered orally, the composition in the combined form is provided with protection from being broken down by amylase and/or other intestinal enzymes and conditions. The protection may be provided by providing linking which is not susceptible to being broken by amylase and/or other intestinal enzymes and conditions.

The composition, particularly as a medicinal product, may be provided in one of the following forms: tablets, capsules, powders, granules, microspheres or ointments, creams, foams, solutions, suppositories, injections, lotions and aerosols.

The composition, particularly as a medicinal product, may be provided with one or more excipients, diluents or adjuvants. For instance, one or more fillers, glidants, binders, lubricants, anti-adherents, disintegrants, buffering agents, moisturising agents, preservatives, solvents, solubilising agents, stabilizers.

BRIEF SUMMARY OF THE DRAWINGS

Various embodiments of the invention will now be described, by way of example only and with reference to the accompanying drawings in which:

FIG. 4 shows a Western blot analysis of amylase size distribution showing degradation/cleavage within an infected environment;

FIG. 5 illustrates experimental results showing the concentration difference between infected wound fluid and plasma for the same individual patient across a series of patients;

DETAILED DESCRIPTION

Amylase

Figure 1:
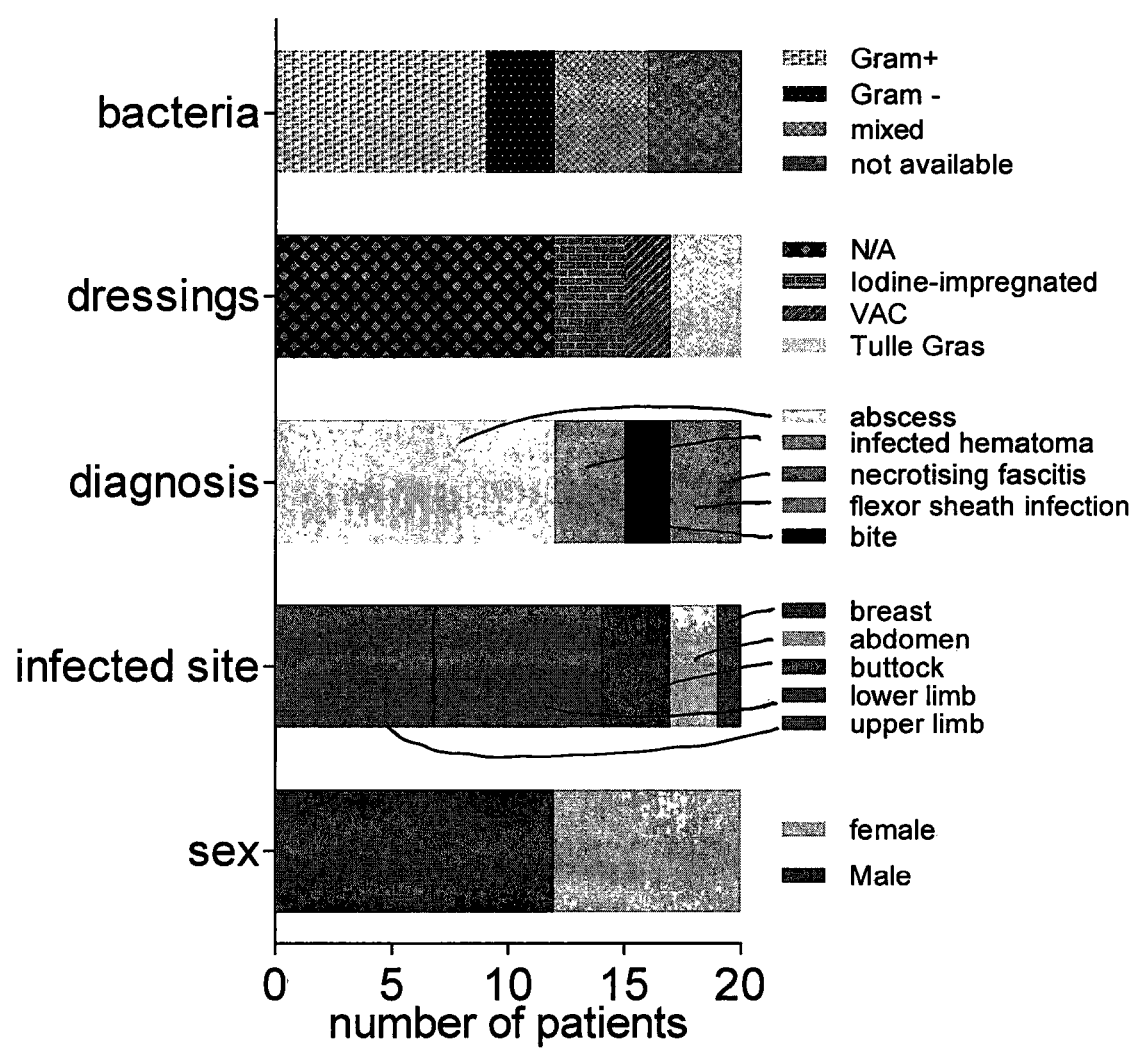
FIG. 1 shows a distribution graph illustrating that detection according to the invention was useful across different types of bacteria, different types of wound, wound dressing, antibiotics, wound site, and depth.

Amylase is a naturally produced enzyme which provides for the breakdown of components in foodstuffs consumed by humans, other animals, together with some plants and bacteria. The enzyme acts by catalysing the hydrolysis of the starches present into sugars. Other enzymes then convert those components to glucose to provide an energy source.

The amylase may be generated by salivary, mammary and lacrimal glands and, in the case of a particular isoform in the pancreas. It occurs naturally in humans, animals, plants, fungi and bacteria. More properly this is α-amylase. α-amylase is also known as 1,4-α-D-glucan glucanohydrolase or glycogenase.

In contrast, β-amylase is naturally produced by bacteria, fungi and plant seeds and so may be present in consumed foodstuffs. β-amylase is also known as 1,4-α-D-glucan maltohydrolase. γ-amylase is primarily found in yeast and fungi, but is also naturally produced in some human tissues, particularly within the intestine. γ-amylase is also known as 1,4-α-D-glucan glucohydrolase.

Amylase is known to be an aid to diagnosis, for instance through test blood serum, urine or peritoneal fluid for hyperamylasemia with a view to informing on acute inflammation of the pancreas.

More recently, amylase, particularly α-amylase, has been used clinically in pancreatic enzyme replacement therapy and other treatments.

Detection and Quantification of Amylase

A variety of sensors or other forms of assay are known which can detect amylase in samples, however, they function by detecting the activity of amylase. They do not operate through the detection of concentration, are not capable of the detection of the concentration levels of amylase typically encountered in medical situations and samples and do not have the necessary sensitivity to detect very low concentration levels of amylase in samples. Furthermore, their response is non-linear in some body fluids, with variation in response to the same activity between body fluids. A sensor offering this combination of features is not available in the prior art.

Activity based detection can be negatively affected by deviation on pH away from the 6.7 to 7.0 range optimal for activity and/or due to temperature and/or due to ionic composition and/or due to the composition of the fluid and/or due to reactions, such as chelation, reducing activity.

In later sections, a sensor is described which allows for the accurate detection of low concentrations of amylase in samples.

Initially, however, a use of such a sensor will be described. The use is in the detection of amylase, more specifically the determination of the concentration of amylase, present in a sample so as to inform on the presence of infection at a site associated with the source of the sample. This is a new pattern of amylase distribution, as compared with the four known patterns; pancreatic, salivary, macroamylasemia and combinations of those three.

The applicant has established that this new pattern of amylase distribution is valid and applicable through the following testing.

A library of infections was compiled to represent a variety of patient sex, infection locations, bacteria identities, dressing type and diagnosis. In the illustrated example of FIG. 1, this was formed of the information from 20 patients. The spread of factors was used to investigate whether the new pattern was applicable to a wide variety of different infections, in terms of organism, site, open and closed wounds, superficial and deep infections and the like.

Samples were collected from infection sites and tested using a sensor described further below. Samples were also collected from plasma simultaneously off each patient and tested in the same manner and using the same sensor. Plasma amylase was used as the comparator. Whilst amylase is present in plasma, the levels are regulated. Infection causes enhanced vascular permeability, therefore, large molecules such as amylase are likely to sequester to the site and not be able to drain away because of distorted lymphatics. Amylase is also likely to be secreted by some bacteria.

Figure 2:
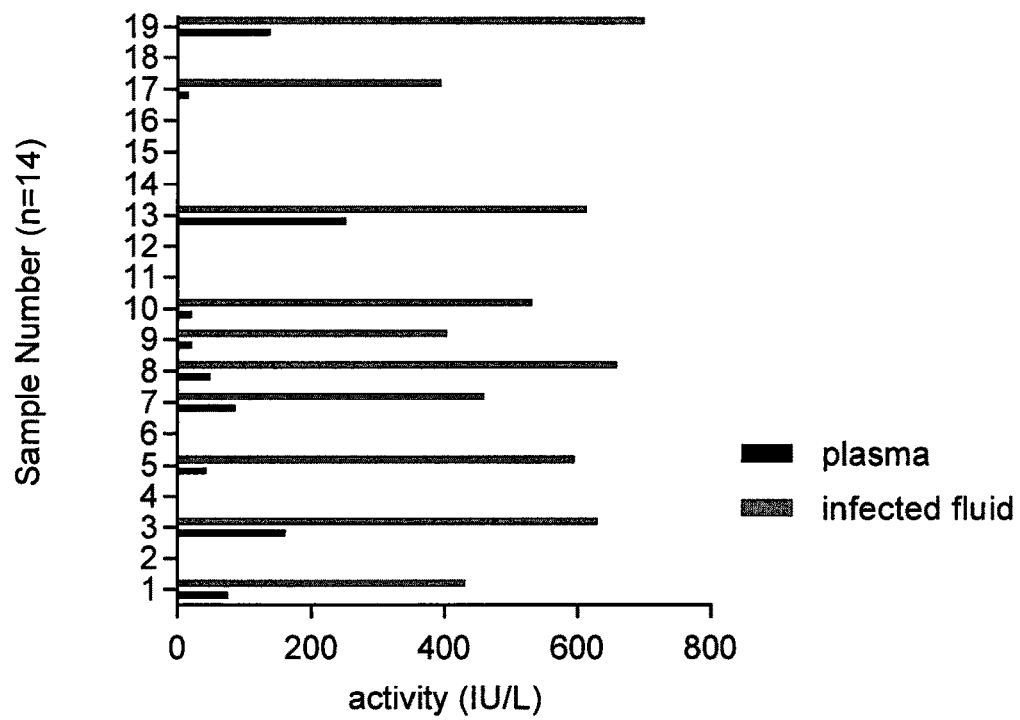
FIG. 2 illustrates experimental results showing the amylase activity for a series of samples, the samples being characterised into the group type "plasma" or the group type "infected fluid"

FIG. 2 shows the amylase activity detected for each of the samples collected. Some samples were of insufficient volume for testing and are shown as absent data points. Testing was possible for 14 samples. FIG. 2 shows whether these were sample associated with an infection site or plasma. The site being infected was established to be true through alternative testing approaches.

Amylase is normally present in human plasma. A substantial difference between the plasma and the infected fluid sample collected off each of the 20 patients was that amylase was detected in each and every one of the infected fluid samples. Many of the plasma samples showed undetectably low concentrations of amylase.

The results of FIG. 2 suggest a marked difference in the amylase activity between plasma samples, where infection is absent, and infection sites, where infection was present.

Figure 3A:
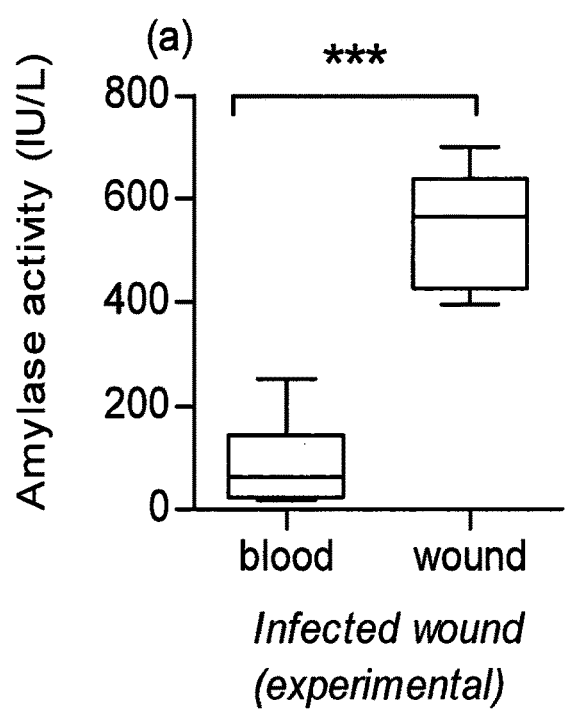
FIG. 3A illustrates the difference in results for the two groups of FIG. 2 using the Mann Whitney matched pairs signed test (P=0.002)
Figure 3B:
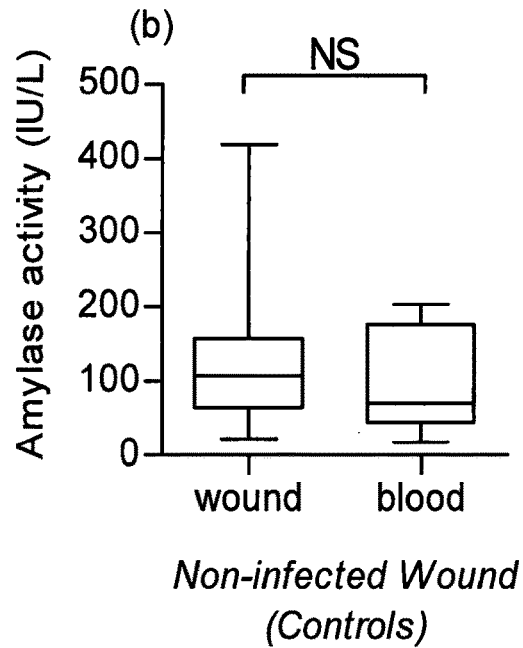
FIG. 3B illustrates the minor differences in results for the groups wound sourced sample and blood sourced sample.
Figure 3C:
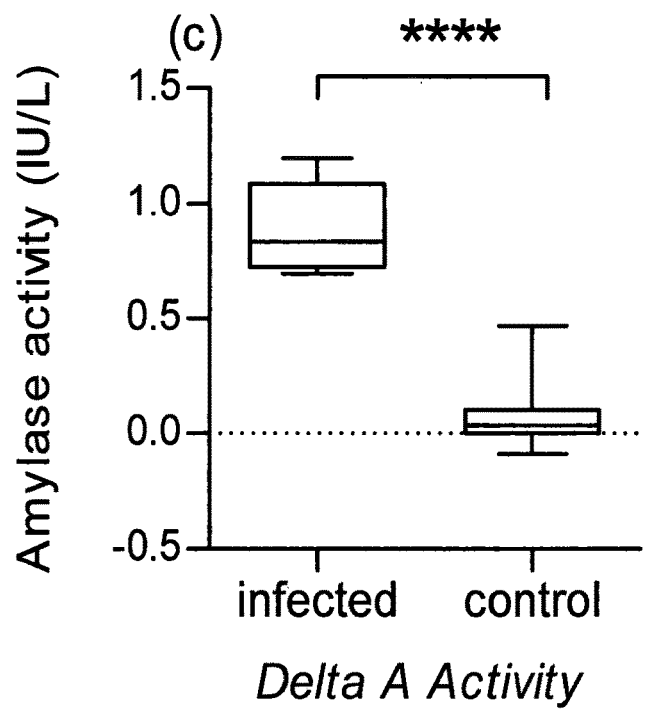
FIG. 3C illustrates the differences in results between the "infected fluid" group of FIG. 2 and a series of control samples.

FIG. 3A shows the outcome when Wilcoxon matched pairs signed rank testing is applied to the results. A separate between the two sample group types is establish with P=0.002. FIG. 3B shows the amylase activity comparison between wound sourced control samples and blood sourced control samples (p=0.3846). FIG. 3C shows the amylase activity comparison between patients providing infected samples and patients providing non-infected samples (p<0.0001, n=20). In FIGS. 2, 3A, 3B and 3C an activity difference is under consideration.

FIG. 4 shows the results from Western blot analysis of amylase size (kDa) distribution from a variety of samples and is indicative of cleavage/degradation of the amylase occurring.

FIG. 5 considers the concentration difference for pairs of results, one of the pair being a plasma sample and the other being an infected site sample taken from the same patient. 20 sample pairs were considered in this case consistent with the patients in the library of FIG. 1. FIG. 5 shows that the difference in concentration between the two samples from the same patient is significant in each and every case tested; 100% increase in concentration in the infected sample in many cases. The sensor showed excellent sensitivity (98%) and high specificity (90%) with respect to infection in the measurement results generated. Sensitivity being the ability to correctly identify those with the infection (true positive rate); specificity being the ability to test correctly to identify those without the infection (true negative rate).

Figure 6:
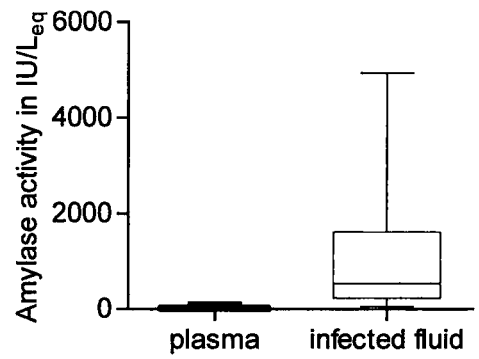
FIG. 6 illustrates the concentration difference in the results for the two groups using the Mann Whitney matched pairs signed test (P<0.0001)

In FIG. 6 the outcome from the application of Mann Whitney matched-pairs signed rank testing is seen. The separation between the two sample types is clearly established with P<0.0001.

Figure 7A:
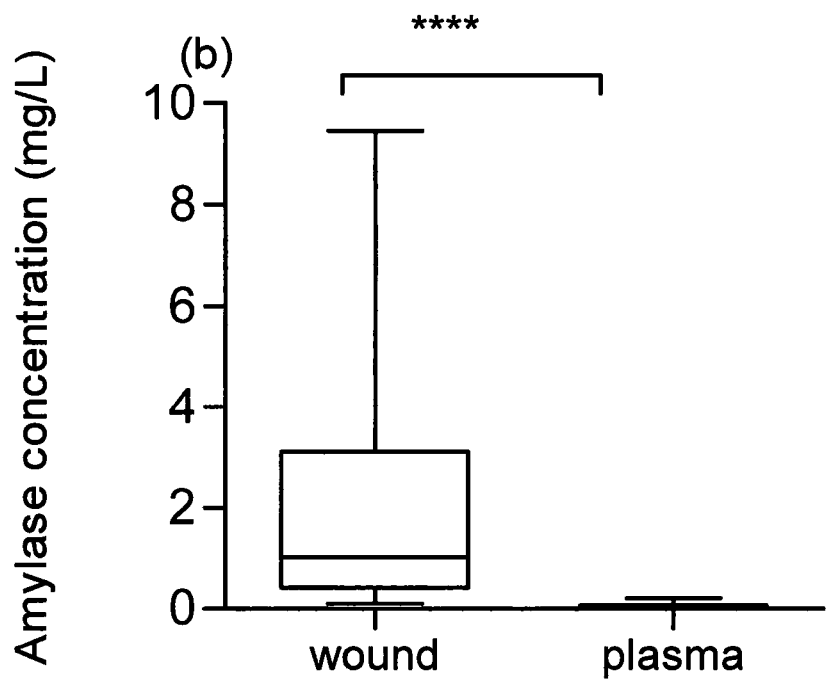
FIG. 7a illustrates the concentration difference (wound/plasma) for infected cases, showing a highly significant difference.
Figure 7B:
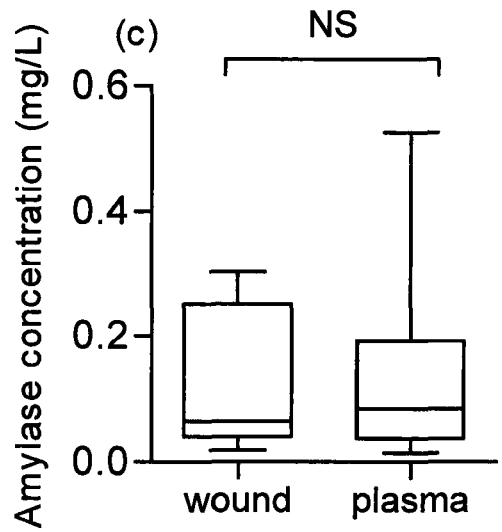
FIG. 7b illustrates the concentration difference (wound/plasma) for non-infected cases, showing no significant difference.
Figure 7C:
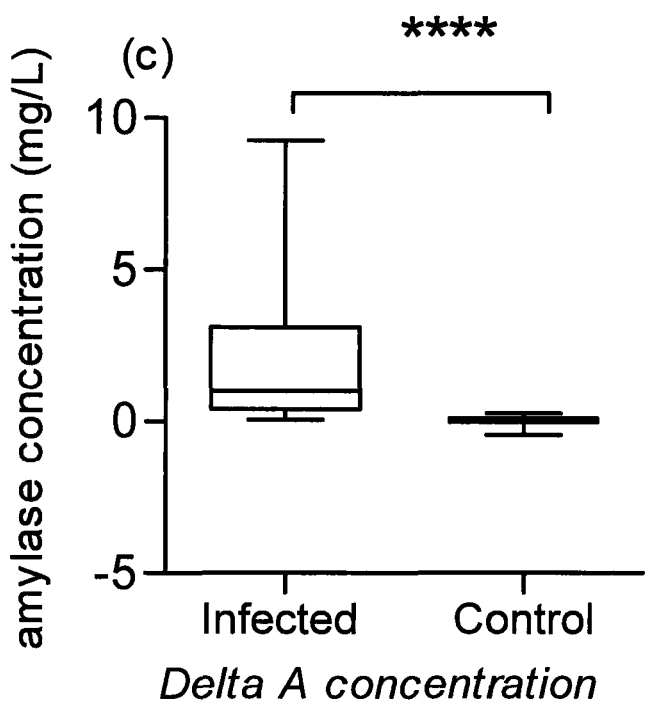
FIG. 7c illustrates the concentration difference between experimental cases and controls, showing a highly significant difference.
Figure 8A:
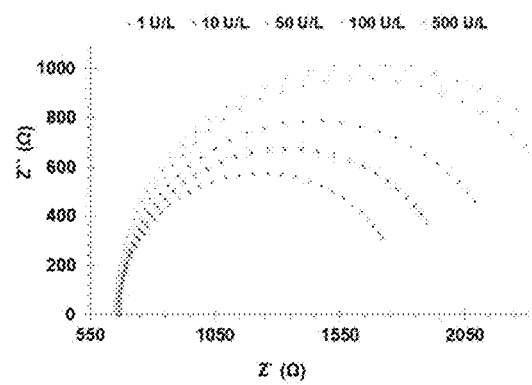
FIG. 8A provides a Nyquist plot showing the effective response of an immunosensor, suitable for use in the present invention, to increasing amylase concentrations.
Figure 8B:
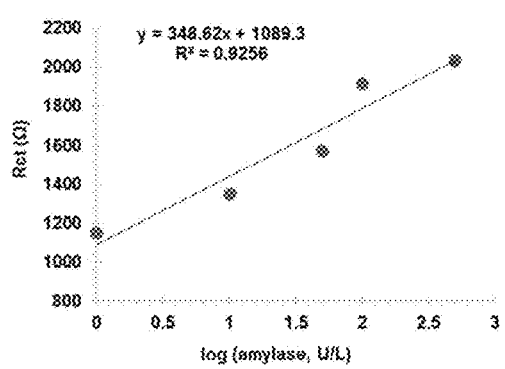
FIG. 8B shows the resulting EIS calibration curve for the immunosensor of FIG. 6A to increasing amylase concentrations.

FIGS. 7a, 7b and 7c show the outcome from the application of Mann Whitney matched pair signed rank testing. With FIG. 7a being infected cases, FIG. 7b being non-infected cases and FIG. 7c controls.

The results show that the difference in amylase between a site of interest and intravascular fluid (defined above) can be used to determine the presence of infection, or its likelihood, at the site of interest. If the activity difference (site of interest versus intravascular fluid) is considered, the distinction is statistically significant. If the concentration is considered, then the distinction is highly statistically significant. The amylase difference between infected and non-infected sites is highly sensitive to the presence of infection.

The experimental results show that the detection of activity and more usefully concentration difference reveals whether or not infection is present at the site. This information could be used to direct subsequent and further investigations. For instance, a determination as to the nature of the infection could be sought, for instance by microbial culture, microscopy, biochemical testing, molecular testing, immunoglobulin binding to amylase or others. This information on the infection can be combined with information on the incident or procedure leading to the wound and then used by a medical practitioner to diagnose a medical condition and the form of treatment appropriate.

A significant benefit of being able to establish that infection is present at the wound site and needs treatment is that no treatment need be given where no infection is established to be present. At the moment, clinical practice errs on the side of caution and so antibiotics, as infection treatment, are administered in most situations. This represents unnecessary antibiotic use and so contributes to wasted costs and, more significantly, increased build-up of resistance to antibiotics.

The applicant has established that this new pattern of amylase distribution is valid and applicable for detecting infection at sites.

In terms of the mechanism by which amylase distribution arises at the site of infection, then there are various possibilities. Amylase which is occurring naturally in the body and distributed throughout the body could be caused to collect at the infection site.

One way this could be caused to happen is through enhanced vascular permeability, and reduced lymphatic clearance: (the so-called enhanced permeability and retention effect). Histamine release has been reported to stimulate amylase secretion and increase vascular permeability, thereby augmenting the EPR effect.

However, the significant, selective and specific sequestration of amylase to a focus of infection reported herein is to a greater extent than seems explained by the EPR effect.

Potentially, the effect is suggested to be due to invasive infection being accompanied by constant bradykinin production which amplifies the limited enhanced vascular permeability observed in non-specific infection, such as that produced in a surgical insult.

The applicant's view is that the most plausible mechanism is that once in this pharmacokinetic compartment that amylase complexes immunoglobins, resulting in entrapment. The applicant references this as Microbe-Associated Large Molecule Trapping and Aggregation phenomenon, MaLTA phenomenon.

Finally, certain classes of micro-organisms secrete amylase themselves, for example *C. perfringens* (a cause of gas gangrene), *C. tetanii* (tetanus), *C. difficile* (hospital acquired pseudomembranous colitis) and *B. cereus* (food poisoning) are all within the *Bacillus* and *Clostridium* genus and those are known to be capable of prolific amylase secretion and so may cause the observed increased amylase levels around infected sites, potentially several orders of magnitude higher.

The mechanism by which the amylase sequesters to the infection site is not material to the invention. The invention has demonstrated that this effect is medically indicative of infection and makes use of it, irrespective of the mechanism of sequestration, to produce clinically useful results.

Initial results show that the use of amylase as a biomarker of infection at sites is a robust method and is capable of dealing with the likely variations in pH, calcium and proteolytic activity to be expected at such sites. The use of amylase as a biomarker of infection also seems capable of successful operation in the context of a wide variety of different dressings, including Negative Pressure Wound Therapy, antibiotic treatment, site and anatomical plane, together with severity of infection.

The description above makes it clear that the method and the sensors used are capable of detecting infection at a site.

As an extension of that, it is possible to link the concentration level of amylase observed to the level of infection; higher levels of infection generating higher concentrations of amylase at the site and in the samples.

In a further extension of that method, it is possible to establish the form of the infection which is present. One possibility in this respect is that the body will generate antibodies specific to the infection caused by the specific bacteria which is the cause of the infection. These antibodies have been observed to form complexes of immunoglobulins and amylase. This means that the antibodies specific to the infection will be in the sample taken and so could be identified in parallel with the detection of the amylase concentration.

Amylase has been observed to have the capacity to complex with immunoglobulins. This means that the antibodies specific to the infection will be in the sample taken and so could be identified in parallel with the detection of amylase. In one such embodiment, this could be done via multiplex sensing.

The interaction between the at least a part of the sample and the sensor occurs without the need for the human or animal body from which the sample arises being present and/or without any interaction between the device and the human or animal body which is the source of the sample. The method is provided outside the normal biological context of the sample. The method is performed outside of the human or animal body and distant therefrom. The method is provided in-vitro by the device and the sensor. The invention provides an in vitro diagnostic device. The invention provides in vitro testing for the marker.

Other Applications of the Detection

It has been suggested that pharmaceutical compounds can be introduced to a body in an inactive form, with the inactive form arising because the pharmaceutical compound is linked in some way to another compound which inactivates it. Whilst the inactive form would be administered to the body as a whole, for instance through injection, it could be activated at the site of interest by the activity of the amylase at that site. Thus the inactive form could be designed such that amylase causes it to breakdown or amylase catalyses the breakdown such that the active compound is rendered pharmaceutically active. The analysis of the invention could be used to establish that there is sufficient amylase, by activity and/or concentration, at the site to cause the activation and/or to impact upon the dosage given or delivery method used because of the level of amylase present at the desired release location.

In a similar manner, the transportation of the pharmaceutical compound as part of a combination with amylase (described further in the next section), could be inspected by the analysis of the present invention to detect for the amylase following breakdown and hence the release of the active compound. Verification of the release would be provided.

Using Amylase as a Transportation Mechanism for Pharmaceutical Compounds

Whilst it has been suggested that amylase which is already naturally occurring at a site could be used to turn an inactive form including a pharmaceutical compound into an active form, potentially by releasing the pharmaceutical compound, the applicant has realised that amylase itself could be used as a transportation mechanism.

When a site transitions from a non-infected to an infected site, amylase moves to and accumulates at the site, as established by the applicant above. If that amylase or some portion of it was linked to a pharmaceutical compound, then the pharmaceutical compound would be preferentially transported to the infection site. The same could apply to other sites at which amylase accumulates or is drawn in other disease situations. Thus amylase offers a targeted delivery system in such cases.

Once at the site, release of the pharmaceutical compound would be triggered.

A variety of constructs could be used. The amylase could be linked directly to the pharmaceutical compound. The amylase could be linked to an intermediary which is in turn linked to the pharmaceutical compound.

The linking could be provided using a number of bioconjugate techniques and chemistries, including but not limited to zero-length cross-linkers homo-bifunctional or heterobifunctional spacers which can be non-biodegradable (such as polyethylglycol) or biodegradable; homogenous or heterogenous.

The pharmaceutical compound could be an antibiotic, for instance for treating infection at the site where the amylase accumulates. Other pharmaceuticals could be analgesics, growth factors etc.

Sensor

The sensor employed in the sample testing described above can be generally categorised as a graphene label free immunosensor. In more detail it is a highly sensitive α-amylase immunosensor platform, produced via in situ electropolymerization of aniline onto a graphene support. Electropolymerization has a material role in improving the sensitivity in detection for amylase and providing lower limits of quantification. This is a significant difference when compared with the assembly of other sensors developed for other purposes, such as those disclosed in WO2015/001286. At the same time, excellent reproducibility and stability in detection are provided, as shown in FIGS. 8, 9, 10 and 11. Covalently binding an α-amylase specific antibody to a polyaniline (PANI) layer and controlling device assembly using electrochemical impedance spectroscopy (EIS) provides a highly linear response against α-amylase concentration.

To improve reproducibility of absolute readings using the sensor, when such a graphene sensor is applied, the invention suggests the use of a double sensor where simultaneous or near simultaneous readings are taken, for instance with respect to the plasma versus fluid of interest. This results in a relative scale of the magnitude of the difference, and hence a solution for the problem.

Further detail on the testing of the sensor for this purpose and further detailed information on the construction of the sensor is provided below.

The type of sensor used in the testing of the invention is beneficial when compared with most existing devices. In most cases, such devices are far from being bedside monitoring devices for α-amylase detection. Current α-amylase assays in clinical use are laboratory based, utilize analytical equipment with a large footprint, have an appreciable turn-around time (TAT), measure activity rather than concentration, and are susceptible to hemolysis and inactivation. These substantial limitations restrict further expansion of α-amylase based diagnostics and theranostics into viable clinical practice. No use of the detection of amylase and particularly α-amylase to indicate infection has been made before.

Demonstrations of Sensor Performance

The performance of the sensor was explored in various ways, including: determination of amylase in a blood plasma mimic; determination of amylase in mouse plasma; and determination of amylase in human plasma.

Blood Plasma Mimic

The sensor was tested for its ability to measure amylase concentrations in a phosphate buffered solution that was used as a blood plasma mimic. Increasing amylase concentrations, from 1 to 500 U/L, which covers the clinically relevant range of amylase levels in the human body, were applied to individual sensors. Both Nyquist plots (FIG. 8A) and the resulting EIS calibration curve (FIG. 8B) clearly demonstrate the effective response of the immunosensor to increasing amylase concentrations.

The diameter of the semicircle increased with increasing amylase concentrations demonstrating an increased resistance as a result of increased analyte concentration at the sensor surface. In general, the change in the semicircle diameter is a result of the change in the interfacial charge transfer resistance (Rct); that is, the resistance corresponding to the carrier transfer from the modified electrode to the ferricyanide in the solution. Thus, the observed diameter increase is explained as the adsorption of plasma onto anti-alpha amylase following an antigen-antibody reaction, where the adsorption of plasma effectively blocks the $[Fe(CN)6]^{3-/4-}$ leading to an increase of Rct. The Rct in the Nyquist plot increased linearly with the amylase concentrations. This is as expected because protein structures bound to the surface of an electrode typically act as barriers to electric transfer. The average slope of the Rct versus log [amylase, U/L] was 0.348 KΩ/[amylase, U/L] with an $R^2$ coefficient of determination of 0.93. The limit of detection (LOD) was 0.0025 U/L. This was as expected as protein structures bound to the surface of an electrode typically act as barriers to electric transfer.

Mouse Plasma

Figure 9:
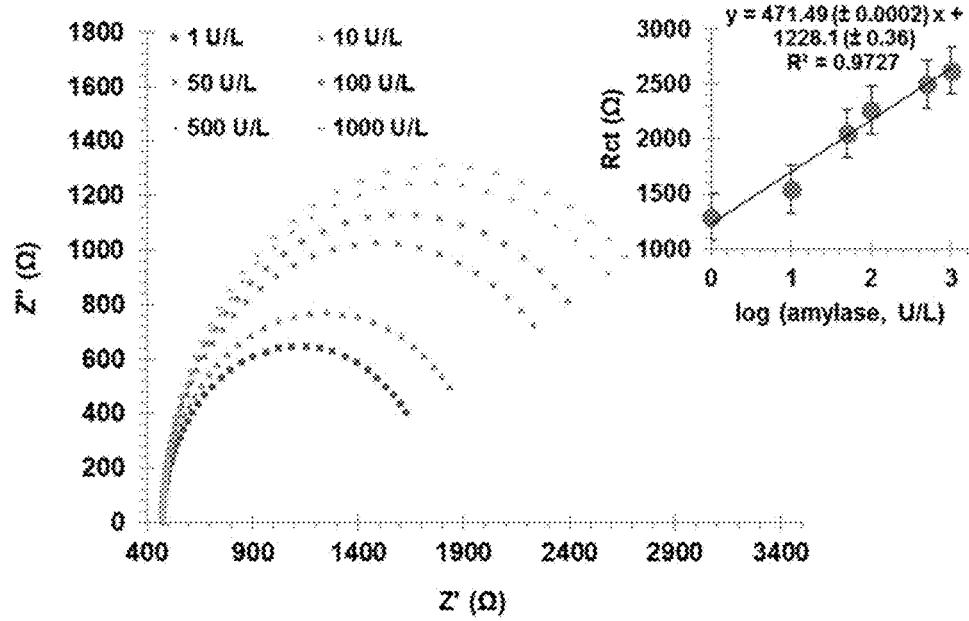
FIG. 9 provides an EIS calibration curve for the immunosensor of FIG. 6A to increasing concentrations of amylase in mouse plasma.
Figure 10:
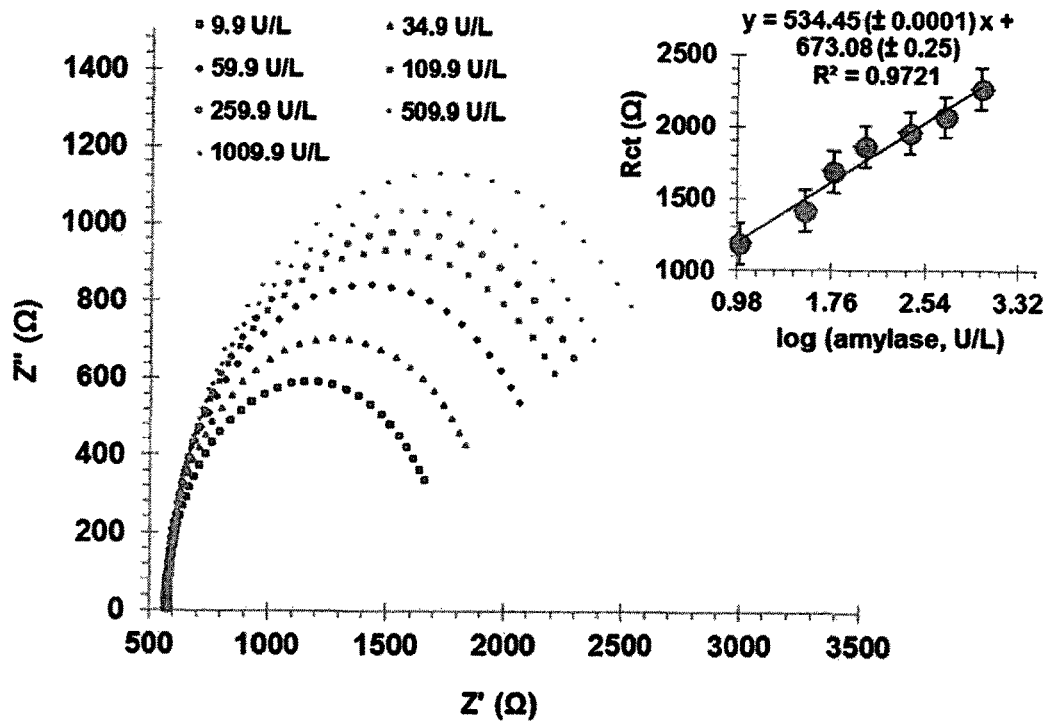
FIG. 10 provides a Nyquist plot showing the dynamic range detectable when the sensor was exposed to various human plasma concentrations (9.9-1009.9 U/L)
Figure 11:
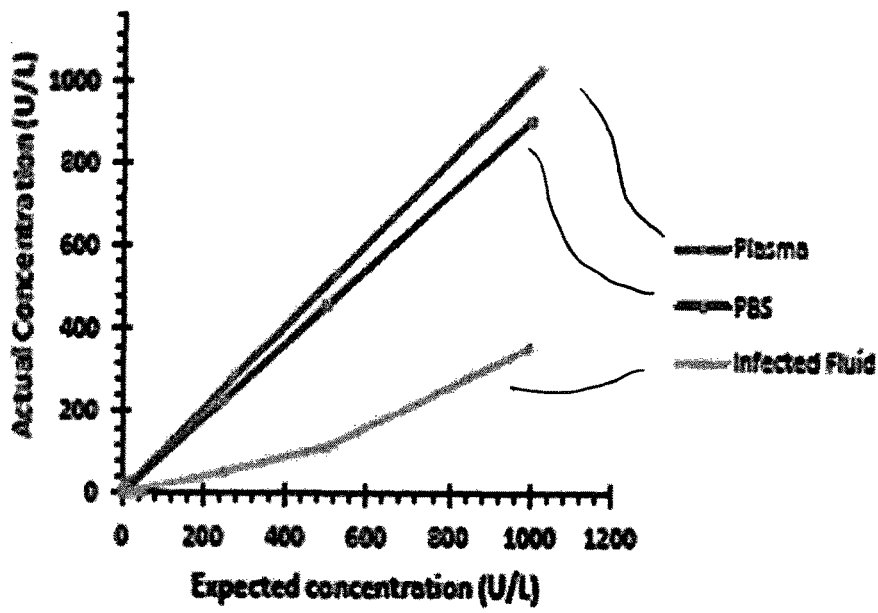
FIG. 11 is a Roche Cobas test or recovery, illustrating linearity of recovery for amylase in plasma and PBS but not linear recovery in infected wound fluid.

In order to demonstrate that the sensor function was effective when exposed to a more complex biological fluid, mouse plasma containing known quantities of amylase were used. α-amylase concentrations were measured in un-spiked and plasma samples with purified human-α-amylase. The linear response ranged from 1 to 1000 U/L and the average slope was of 0.472 KΩ[amylase, U/L]. The EIS calibration curve of the immunosensor in response to increasing concentrations of amylase in mouse plasma showed no adverse effect on sensor performance in the presence of a more complex fluid compared to the PBS (FIG. 9).

Human Plasma

To provide proof of function for a clinically useful device, human plasma samples obtained from a patient suffering with clinical infection were analyzed. By spiking the human plasma with known concentrations of amylase we were able to determine the effectiveness and LOD of the sensor at physiologically relevant analyte concentrations.

Nyquist plots (FIG. 10) of EIS spectra show the dynamic range detectable when the sensor was exposed to various human plasma concentrations (9.9-1009.9 U/L).

Overall, the sensor was demonstrated to offer highly sensitive detection and a remarkably wide limit of quantification (0.025-1000 IU/L) compared to α-amylase assays in current clinical use.

In addition, the sensor had a maximum interval to obtain a result of 300 seconds. This compares very well with existing devices in clinical practice, where, despite turn-around times (TAT) being a key indicator of laboratory performance, the current TAT for clinical assays is around 45 minutes.

Moreover haemolysis, sample inactivation, and the presence of contaminants interfering with colorimetric assays commonly lead to assay failure with current clinical assay systems. Since the system described in this document is label-free, and does not require either colorimetric change, it is reasonable to support the notion that the new technology will not be affected such factors.

Finally, it is worth noting that the results indicate a three-log fold expansion in the lower limit of quantification when compared to current clinical assay systems. This is of interest to forensic medicine where detection of amylase can lead to a DNA profile from saliva, semen or vaginal secretions.

Sensor Construction

Electrochemical impedance spectroscopy (EIS) enables detection and signal output due to its ability to measure subtle changes in the electrochemical properties of materials at their interface with conducting electrodes. Gold, zinc oxide, iron oxide, and carbon are the main substrates that are being developed for use in such sensors, but carbon nanostructures, and graphene, are alternatives to gold as electrode substrates.

Graphene is of particular interest as a biosensor platform due to intrinsic properties such as its large surface area, high electrical conductivity and biocompatibility. Graphene based devices have been developed that can measure minute changes in analyte concentration levels. Composed of $sp^2$ carbon, graphene is chemically unsaturated. Intrinsically, it can undergo covalent addition to change the carbons from $sp^2$ to spa following hybridization, however, carbon atoms in the graphene basal plane are protected by their π-conjugation system, the motion of which is constrained by surrounding carbon atoms. Therefore, basal plane covalent addition usually encounters large energy barriers, and reactive chemical groups, such as atomic hydrogen, fluorine, and precursors of other chemical radicals, are usually needed as reactants. The controlled functional association of biomolecules with graphene is therefore key to developing any high throughput biosensor platform.

Figure 12:
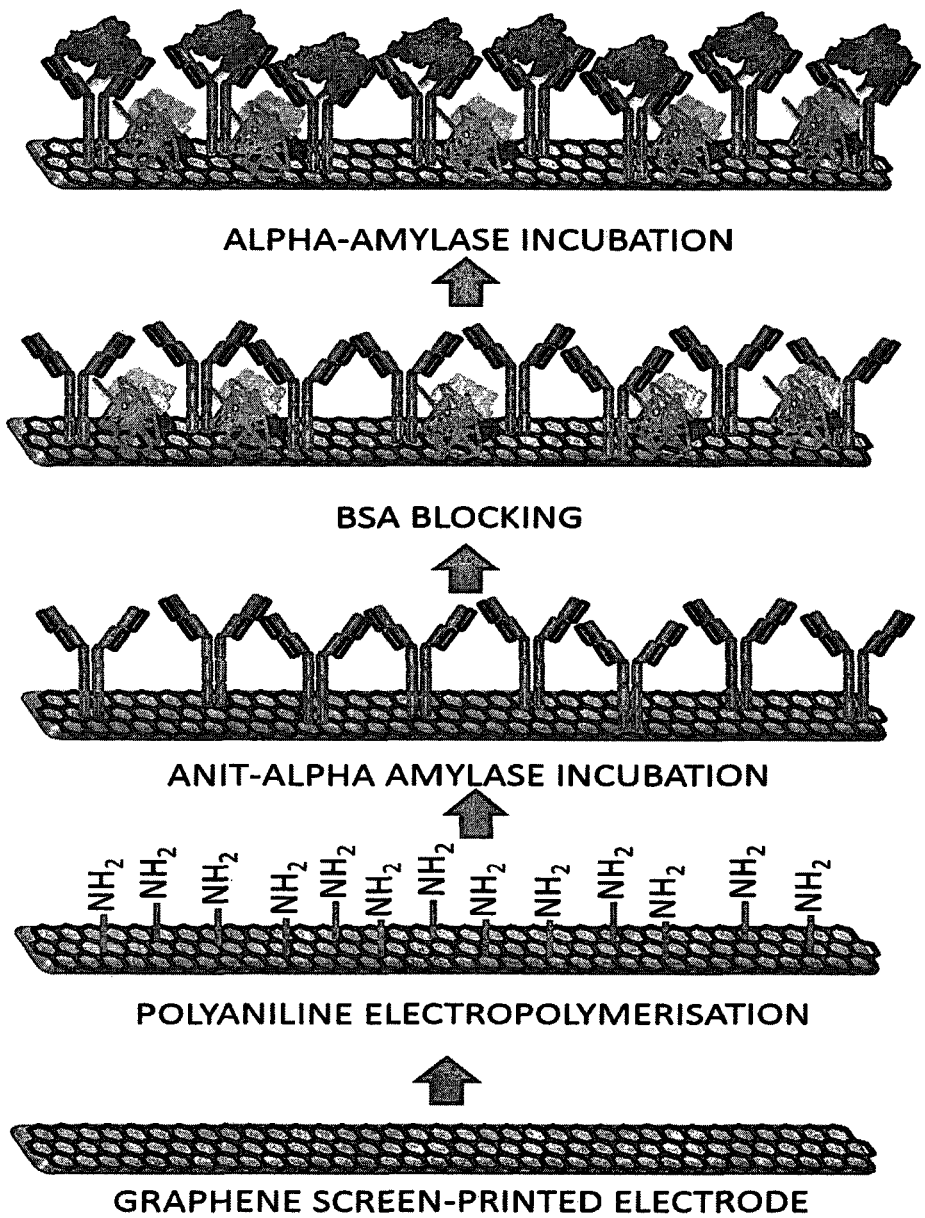
FIG. 12 is a schematic a illustration of the construction of the graphene sensor, including the electropolymerization of polyaniline to the graphene surface.

FIG. 12 provides a schematic illustration of the construction sequence for a suitable sensor.

Polyaniline (PANI) is a conductive polymer and is used as an additive transducer layer in the sensor to avoid the introduction of graphene surface defects. In addition the use of PANI improves antibody attachment to sensor electrodes while preserving optimal electrical characteristics. In addition, PANI has excellent acid/base sensitivity, a huge range of tunable conductivity, redox sensitivity, environmental stability, short reversible response times, and is easily synthesized and functionalized.

The sensor of this document is an α-amylase specific immunosensor, using a combination of electro-polymerization of PANI on a graphene support and subsequent antibody binding to the polymer film.

The selection of electropolymerization has a material role in improving the sensitivity in detection for amylase and providing lower limits of quantification. At the same time, excellent reproducibility and stability in detection are provided, as shown in FIGS. 8, 9, 10 and 11.

The biosensor platform enables fully quantitative analysis of analyte concentrations in a simulated biological sample and in human plasma. The device displays a linear response to increasing α-amylase concentration between 1 and 1000 International Units/L (IU/L), and a LOD of 0.025 U/L. This increased sensitivity arises because of electrochemical deposition.

In construction, a screen-printed graphene electrode was functionalized via polymerization with a thin film of polyaniline to provide amine groups on the graphene/PANI. The PANI film was formed by coating the electrode in a solution of aniline and subsequent electropolymerization to form a conductive polymer layer over the graphene support, enabling the transport of electron carriers to the graphene.

Having deposited polyaniline, the sensor was then functionalized through covalently linking a α-amylase antibody to the PANI layer. A carbodiimide crosslinker chemistry EDAC/NHS was used for the specific activation of the —COOH terminated amino acid chains in the antibody. This forms a highly reactive O-Acylisourea intermediate that rapidly reacts with NHS to produce a stable succinimydyl ester. This ester then undergoes a nucleophilic substitution reaction with the amine groups on the PANI, leading to the formation of an orientated antibody grafted PANI layer. Due to exposure to the EDAC/NHS reagents, it is possible that each of —COOH groups at the antibody may have been activated. It is not possible therefore to ensure exclusive antibody binding through the $F_c$ region, only that orientation via the $F_c$ region is significantly higher than with random antibody adsorption. Bovine serum albumin (BSA) was then added to the sensor surface randomly, and serves to prevent any non-specific interactions with the sensor surface thereby eliminating the possibility of the sensor generating any non-specific background signal.

Whilst the above is an example of a suitable sensor, other suitable sensors capable of detecting amylase activity and more preferably concentration, can be used. These include the sensors disclosed in:

Federal Drug Agency (FDA) 510(k) substantial equivalence determination decision summary device only template (b) Bowling, J. L.; Katayev, A., An evaluation of the Roche Cobas c 111. Lab Medicine 2010, 41 (7), 398-402.

Together with the sensors described in the following table and which are available in clinical practice. AMP=Amperometric, EIS=Electrochemical Impedance Spectroscopy, FAU=Fungal Amylase Unit. FIA=Pow Injection Analysis, KNU=kilo Novo unit, LOD=Limit of Detection, LR=Linear Range, nkat=nanokatals

| Assay | Design | Sequential Process | Detection Technique | Limits of detection | Specificity | Ref. |
|---|---|---|---|---|---|---|
| Rate of product formation | Flow system using a peroxide electrode and enzyme membrane with glucose oxidase, α-glucosidase and optionally mutarotase cross-linked by gelatin-glutaraldehyde | α-glucosidase converts maltose to α-D-glucose. Mutarotase converts α-D-glucose to β-D-glucose which is determined via glucose oxidase | AMP | LOD: 2 nkat/mL (0.117.64 units/mL) when reaction time 5 min 0.5 nkat/mL (0.02941 units/mL) when reaction time 30 min LR: 0.1-3 mmol/L | Any α-amylase | [145] |
| | Screen-printed electrodes with immobilized α-glucosidase, glucose oxidase and mutarotase modified with Prussian Blue | α-glucosidase converts maltose to α-D-glucose. Mutarotase converts α-D-glucose to β-D-glucose which is determined via glucose oxidase | AMP | LOD: 5 units/mL LR: 5-250 units/mL | Any α-amylase | [146] |
| | Flow-injection device using maltopentaose as substrate. α-glucosidase immobilised on pre-activated membrane. Glucose oxidase immobilized on electrode | α-glucosidase converts maltose to 5-d-glucose. Glucose oxidase coverts 5-d-glucose to gluconic acid and hydrogen peroxide which is measured | AMP | LOD: LR: 0-30 units/mL | Any α-amylase | [147] |
| | Spectrophotometric flow injection measuring brick red complex formation at 540 nm | Amylose incubated with sample to produce maltose. 3,5 dinitrosalicylic-acid and maltose boiled | SIA/FIA | LOD: 0.0048 FAU LR: 0.005-0.06 FAU | Any α-amylase | [148] |
| | Use of portable personal glucose meter | Sample, α-glucosidase and maltopentaose incubated 15 min at 37° C. | | LOD: 20 U/L LR: 2.2-27.8 mM | Any α-amylase | [149] |
| | Flat-chip micro analytical sensor used as part of a Micro-Electro-Mechanical Systems. Pre-column and flat-enzyme electrode incorporated into a flow cell where maltose phosphorylase, glucose oxidase and peroxidase immobilised | Maltose phosphorylase phosphorylates maltose. Glucose oxidase converts phosphorylated maltose to gluconic acid and hydrogen peroxide which is measured | Electro-chemical and Lateral flow | LR: 0-190 kU/L | Any α-amylase | [147] |

| Assay | Design | Sequential Process | Detection Technique | Limits of detection | Specificity | Ref. |
|---|---|---|---|---|---|---|
| | Colorimetric assay biosensor system using Gal-G2-CNP, chromogenic substrate for α-amylase. CNP is a yellow product once hydrolysed which can be measured photometrically at 430 nm. | Disposable test strip placed under tongue (25 μl) Once strip inserted into reader and saliva moved onto the reagent paper. The entire test takes roughly 30 sec. | AMP | LR: 10-230 U/mL | Any α-amylase | [150] |
| Rate of starch digestion | Flow injection spectrophotometric analysis based on starch-iodine complexes | Sample degradation of complexes measured in flow channel | FIA | LOD: 60 NU/mL LR: 0.25-5.0 KNU/mL | Any α-amylase | [151] |
| | Immobilized layer of starch gel on thick-film magneto elastic sensor and presence of α-amylase alters the resonance frequency | Sample placed on starch gel | | LR: 75-125 U/mL | Any α-amylase | [152] |
| | Spectrofluorimetric using the quenching of luminescence intensity (634 nm) of nano CdS doped in sol-gel of different concentrations of maltose | Sample incubated with starch in flow channels | FIA | LOD: $5.7 \times 10^{-11}$ mol/L LR: $4.8 \times 10^{-10}$ – $1.2 \times 10^{-5}$ mol/L | Any α-amylase | [153] |
| | Glycogen/amylopectin spin-coated on gold coated quartz crystals (case frequency of 10 MHz). Films cross-linked with hexamethylene diisocyanate. Film degradation measured with quartz crystal microbalance | Sample incubated with film | EIS | | Any α-amylase | [154] |
| | Degradation of starch-triiodide measured using platinum redox sensor for direct potentiometric determination | Sample incubated with starch-triiodide | | LOD: 1.944 mU LR: 0-0.54 U | Any α-amylase | [155] |
| | Glucose oxidase-based biosensor measuring the decrease in dissolved oxygen concentration related to starch concentration. Glutaraldehyde as a cross-linker | | | LOD: LR: 0.66-9.83 U/mL | Any α-amylase | [156] |
| Antibody to antigen | Layer of salivary antibody on Au-electrode and interactions monitored by an electroactive indicator ($K_3Fe(CN)_6$). | The electroactive was oxidized or reduced depending on concentration of salivary α-amylase present | AMP | LOD: 1.57 pg/mL LR: 0.003-0.016 ng/mL | Human salivary α-amylase | [113] |

The invention claimed is:

1. A method of indicating the presence of a bacterial infection in a biological sample obtained from a wound of a subject, other than a pancreatic wound or oral digestive wound, the method comprising:

a. providing a device comprising a biosensor, wherein the biosensor includes an α-amylase specific antibody and an interaction arises between the α-amylase specific antibody and α-amylase when the α-amylase is present in the biological sample;

b. contacting at least a part of the biological sample with the biosensor of the device;

c. analysing the at least a part of the biological sample with respect to the α-amylase by detecting for the interaction between the α-amylase specific antibody and the α-amylase;

d. indicating an amount of the α-amylase present in the biological sample using the device;

e. repeating steps b.-d. on a blood, plasma, or serum sample obtained from the subject, thereby indicating an amount of α-amylase present in the blood, plasma, or serum sample; and f. comparing the amount of α-amylase in the biological sample with the amount of α-amylase in the blood, plasma, or serum sample, and where the difference in the amount of α-amylase in the biological sample compared with that in the blood, plasma, or serum sample is elevated above 140 IU/L, concluding the elevated amount of α-amylase is indicative of a bacterial infection present in the biological sample.

2. The method according to claim 1, wherein the method is a method of diagnosing infection.

3. The method according to claim 1, wherein the method is a method of quantifying the amount of α-amylase in the at least a part of the biological sample and the blood, plasma, or serum sample.

4. The method according to claim 1, wherein the method is a method of quantifying the concentration of α-amylase and/or the activity of α-amylase in the biological sample relative to the concentration and/or activity of α-amylase in the blood, plasma, or serum sample.

5. The method according to claim 1, wherein the wound is one or more of: a breast, abdomen, buttocks, lower limb, or upper limb wound.

6. The method according to claim 1, wherein the device further comprises one or more or all of: a power source; control electronics; a computer processor; computer memory; a user interface; a user viewable display; a signal output connection; and a signal input connection.

7. The method according to claim 1, wherein the biosensor is: screen printed on to a part of the device; and/or is a graphene based sensor; and/or includes electropolymerization of a component of the biosensor.

8. The method according to claim 1, wherein the biosensor comprises an electrochemical impedance spectroscopy sensor.

9. The method according to of claim 1, wherein the biosensor has a linear response against α-amylase concentration and/or detects concentrations of α-amylase as low as 100 International Units/L (IU/L).

10. The method according to claim 1, wherein the biosensor detects concentrations of α-amylase as low as 1 International Units/L (IU/L).

11. The method according to claim 1, wherein the biosensor has a limit of detection as low as 0.025 U/L.

12. The method according to claim 1, wherein the subject is treated for infection when the amount of α-amylase is elevated in the biological sample compared with that in the blood, plasma, or serum sample.

13. The method according to claim 1, wherein the subject is not treated for infection when the amount of α-amylase is not elevated in the biological sample compared with that in the blood, plasma, or serum sample.

14. The method according to claim 1, wherein the biological sample is a fluid sample obtained from the wound.

15. The method of claim 1, wherein the wound is a torso or limb wound.

16. The method of claim 1, wherein the wound is not contaminated with salivary amylase.

17. The method of claim 1, where the amount of α-amylase in the biological sample is at least 400 IU/L.

18. A method of indicating the presence of a bacterial infection in a biological sample obtained from a wound of a subject, wherein the wound is not associated with a known pancreatic, salivary, or macroamylasemia pattern of amylase distribution, the method comprising:
   a. providing a device comprising a biosensor, wherein the biosensor includes an α-amylase specific antibody and an interaction arises between the α-amylase specific antibody and α-amylase when the α-amylase is present in the biological sample;
   b. contacting at least a part of the biological sample with the biosensor of the device;
   c. analysing the at least a part of the biological sample with respect to the α-amylase by detecting for the interaction between the α-amylase specific antibody and the α-amylase;
   d. indicating an amount of the α-amylase present in the biological sample using the device;
   e. repeating steps b.-d. on a blood, plasma, or serum sample obtained from the subject, thereby indicating an amount of α-amylase present in the blood, plasma, or serum sample; and
   f. comparing the amount of α-amylase in the biological sample with the amount of α-amylase in the blood, plasma, or serum sample, and where the difference in the amount of α-amylase in the biological sample compared with that in the blood, plasma, or serum sample is elevated above 140 IU/L, concluding the elevated amount of α-amylase is indicative of a bacterial infection present in the biological sample.

19. The method of claim 18, where the amount of α-amylase in the biological sample is at least 400 IU/L.

\* \* \* \* \*